(12) United States Patent
Graveley

(10) Patent No.: US 12,702,810 B2
(45) Date of Patent: Aug. 11, 2026

(54) HYBRID CONNECTOR FOR INTRAVASCULAR IMAGING DEVICES

(71) Applicant: Boston Scientific Scimed, Inc., Maple Grove, MN (US)

(72) Inventor: Andrew Brian Graveley, Shoreview, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 186 days.

(21) Appl. No.: 18/622,138

(22) Filed: Mar. 29, 2024

(65) Prior Publication Data

US 2024/0325713 A1 Oct. 3, 2024

Related U.S. Application Data

(60) Provisional application No. 63/455,488, filed on Mar. 29, 2023.

(51) Int. Cl.
*A61M 39/10* (2006.01)
*A61B 90/00* (2016.01)

(52) U.S. Cl.
CPC ........... *A61M 39/10* (2013.01); *A61B 90/361* (2016.02); *A61B 2090/3614* (2016.02)

(58) Field of Classification Search
CPC ................. A61M 39/10; A61B 90/361; A61B 2090/3614; A61B 5/0066; A61B 5/0084;
(Continued)

(56) References Cited

U.S. PATENT DOCUMENTS 4,841,977 A 6/1989 Griffith et al.
5,375,602 A 12/1994 Lancee et al.
(Continued)

FOREIGN PATENT DOCUMENTS

CN 109044404 A 12/2018
EP 2679167 A1 1/2014
(Continued)

OTHER PUBLICATIONS

International Search Report and Written Opinion dated Dec. 19, 2018 for International Application No. PCT/US2018/052685.
(Continued)

*Primary Examiner* — Joel Lamprecht
(74) *Attorney, Agent, or Firm* — Seager, Tufte & Wickhem, LLP

(57) ABSTRACT

Intravascular imaging systems and methods for making and using intravascular imaging devices are disclosed. An example intravascular imaging device may include an imaging catheter. An imaging core may be translatable and rotatable within the imaging catheter. The imaging core may include a first imaging device and a second imaging device different from the first imaging device. A connector assembly may be disposed adjacent to a proximal end region of the imaging catheter. The connector assembly may be configured to connect the imaging catheter to a control unit. The connector assembly may include a first connector for connecting the first imaging device to the control unit and a second connector for connecting the second imaging device to the control unit. The connector assembly may be spring-loaded.

20 Claims, 9 Drawing Sheets

(58) Field of Classification Search
CPC ..... A61B 8/4416; A61B 8/445; A61B 8/4461; A61B 8/12; G02B 6/3817; G02B 6/3821
See application file for complete search history.

(56) References Cited

U.S. PATENT DOCUMENTS 5,643,297 A 7/1997 Nordgren et al.
5,772,609 A 6/1998 Nguyen et al.
6,004,271 A 12/1999 Moore
6,139,510 A 10/2000 Palermo
6,292,681 B1 9/2001 Moore
6,945,938 B2 9/2005 Grunwald
6,966,891 B2 11/2005 Ookubo et al.
7,037,271 B2 5/2006 Crowley
7,246,959 B2 7/2007 Nakatani
7,306,561 B2 12/2007 Sathyanarayana
7,622,853 B2 11/2009 Rehrig et al.
7,625,367 B2 12/2009 Adams et al.
7,666,143 B2 2/2010 Wilser et al.
8,062,226 B2 11/2011 Moore
8,114,032 B2 2/2012 Ferry et al.
8,147,414 B2 4/2012 Abraham
8,317,711 B2 11/2012 Dala-Krishna
8,323,203 B2 12/2012 Thornton
8,403,856 B2 3/2013 Corl
8,523,778 B2 9/2013 Sadaka
8,728,010 B2 5/2014 Hirshman
8,932,223 B2 1/2015 Emelianov et al.
9,084,575 B2 7/2015 Moore et al.
9,474,506 B2 10/2016 Magnin et al.
9,839,410 B2 12/2017 Courtney et al.
9,872,665 B2 1/2018 Okubo et al.
9,895,163 B2 2/2018 Trovato
9,931,101 B2 4/2018 Okubo et al.
10,039,522 B2 8/2018 Magnin et al.
10,052,082 B2 8/2018 Oliver et al.
10,076,272 B2 9/2018 Devgon et al.
10,130,337 B2 11/2018 Okubo et al.
10,130,427 B2 11/2018 Tanner et al.
10,143,411 B2 12/2018 Cabot
10,204,718 B2 2/2019 Williams et al.
10,420,456 B2 9/2019 Zelenka et al.
10,420,530 B2 9/2019 Hancock et al.
10,448,922 B2 10/2019 Van Hoven et al.
10,485,608 B2 11/2019 Moisa et al.
10,492,757 B2 12/2019 Sakaguchi
10,555,780 B2 2/2020 Tanner et al.
10,575,819 B2 3/2020 Davies et al.
10,758,207 B2 9/2020 Park et al.
10,779,796 B2 9/2020 Hiltner et al.
10,792,012 B2 * 10/2020 Hutchins .................. A61B 8/12
10,905,851 B2 2/2021 Zelenka et al.
10,932,752 B2 3/2021 Sakaguchi
10,993,694 B2 5/2021 Meyer et al.
11,076,829 B2 8/2021 Okubo et al.
11,213,356 B2 1/2022 Tanner et al.
12,127,881 B2 * 10/2024 Hutchins .............. A61B 5/0084
2003/0097072 A1 5/2003 Serrano et al.
2004/0108789 A1 6/2004 Marshall
2004/0181174 A2 9/2004 Davis et al.
2005/0124857 A1 6/2005 Adams et al.
2005/0143664 A1 6/2005 Chen et al.
2005/0215942 A1 9/2005 Abrahamson et al.
2006/0058622 A1 3/2006 Tearney et al.
2006/0084875 A1 4/2006 Knight
2006/0100522 A1 5/2006 Yuan et al.
2006/0106320 A1 5/2006 Barbato
2006/0173350 A1 8/2006 Yuan et al.
2006/0253028 A1 11/2006 Lam et al.
2007/0016054 A1 1/2007 Cao et al.
2007/0038111 A1 2/2007 Rehrig et al.
2007/0083119 A1 4/2007 Adachi et al.
2007/0167827 A1 7/2007 Masters
2009/0156941 A1 6/2009 Moore
2009/0163817 A1 6/2009 Masters et al.
2009/0264769 A1 10/2009 Sadaka
2009/0270737 A1 10/2009 Thornton
2010/0098380 A1 4/2010 Gordon et al.
2010/0249603 A1 9/2010 Hastings et al.
2010/0280316 A1 11/2010 Dietz et al.
2011/0071400 A1 3/2011 Hastings et al.
2011/0098573 A1 4/2011 Thornton et al.
2011/0207995 A1 8/2011 Snow et al.
2012/0059241 A1 3/2012 Hastings et al.
2012/0197113 A1 8/2012 Courtney et al.
2012/0253197 A1 10/2012 Sadaka
2013/0079642 A1 3/2013 Marshall et al.
2013/0216114 A1 8/2013 Courtney et al.
2013/0331706 A1 12/2013 Hossack et al.
2014/0142432 A1 5/2014 Hutchins et al.
2014/0171804 A1 6/2014 Van Hoven
2014/0180031 A1 6/2014 Anderson
2014/0180127 A1 6/2014 Meyer et al.
2015/0196285 A1 7/2015 Mori
2015/0359510 A1 12/2015 Currlin et al.
2016/0302762 A1 10/2016 Stigall et al.
2016/0324503 A1 11/2016 Norris et al.
2017/0164925 A1 6/2017 Marshall et al.
2018/0280680 A1 10/2018 Isaacson et al.
2018/0368934 A1 12/2018 Van Der Linde et al.
2019/0151128 A1 5/2019 Cohen et al.
2019/0357879 A1 11/2019 Corl
2020/0029855 A1 * 1/2020 Hayes .................. A61B 5/6851
2020/0086086 A1 3/2020 Barone et al.
2020/0100764 A1 4/2020 Sakaguchi
2020/0129149 A1 4/2020 Tokida et al.
2020/0187904 A1 6/2020 Davies et al.
2020/0275909 A1 9/2020 Mniece et al.
2021/0128109 A1 5/2021 Groenland et al.
2021/0298718 A1 9/2021 Saroha et al.
2021/0338199 A1 11/2021 Sakaguchi
2022/0015740 A1 1/2022 Sakaguchi
2022/0361743 A1 11/2022 Chan et al.
2023/0309962 A1 10/2023 Nguyen et al.
2023/0355206 A1 11/2023 Butler et al.

FOREIGN PATENT DOCUMENTS

EP 2832295 A1 2/2015
JP 2005177205 A 7/2005
JP 20110152274 A 8/2011
JP 2016501079 A 1/2016
WO 9956627 A1 11/1999
WO 2005056096 A1 6/2005
WO 2009009802 A1 1/2009
WO 2009048339 A1 4/2009
WO 2009073752 A1 6/2009
WO 2009079569 A2 6/2009
WO 2009108863 A1 9/2009
WO 2009121067 A1 10/2009
WO 2014100606 A1 6/2014

OTHER PUBLICATIONS

International Search Report and Written Opinion dated Jun. 16, 2023 for International Application No. PCT/US2023/015502.
International Search Report and Written Opinion dated Aug. 3, 2023 for International Application No. PCT/US2023/021155.
International Search Report and Written Opinion dated Jul. 17, 2023 for International Application No. PCT/US2023/016738.
International Search Report and Written Opinion for International Application No. PCT/US2023/082505 dated Feb. 14, 2024.
International Search Report and Written Opinion for International Application No. PCT/US/2024/022323, dated Jul. 17, 2024. (12 pages).

* cited by examiner 10
12
14
16
20
22
24
25
25
25
26
28
30
32
34
36

75
74
85
77
76
70
69
52
56
71
48
68
67

HYBRID CONNECTOR FOR INTRAVASCULAR IMAGING DEVICES

CROSS-REFERENCE TO RELATED APPLICATIONS

This application claims the benefit of priority under 35 U.S.C. § 119 of U.S. Provisional Application No. 63/455,488, filed Mar. 29, 2023, the entire disclosure of which is hereby incorporated by reference.

TECHNICAL FIELD

The present disclosure pertains to medical devices, and methods for manufacturing medical devices. More particularly, the present disclosure pertains to intravascular imaging devices.

BACKGROUND

A wide variety of medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An intravascular imaging system is disclosed. The intravascular imaging devices comprises: an imaging catheter; an imaging core translatable and rotatable within the imaging catheter; wherein the imaging core includes a first imaging device and a second imaging device different from the first imaging device; a connector assembly disposed adjacent to a proximal end region of the imaging catheter, the connector assembly being configured to connect the imaging catheter to a control unit; wherein the connector assembly includes a first connector for connecting the first imaging device to the control unit and a second connector for connecting the second imaging device to the control unit; and wherein the connector assembly is spring-loaded.

Alternatively or additionally to any of the embodiments above, the first imaging device includes an ultrasound transducer.

Alternatively or additionally to any of the embodiments above, further comprising an electrical conductor coupled to the ultrasound transducer and extending to the first connector.

Alternatively or additionally to any of the embodiments above, the first connector includes one or more electrical pins.

Alternatively or additionally to any of the embodiments above, the second imaging device includes an optical imaging device.

Alternatively or additionally to any of the embodiments above, further comprising an optical fiber coupled to the optical imaging device and extending to the second connector.

Alternatively or additionally to any of the embodiments above, the second connector includes a ferrule and a connecting sleeve disposed about the ferrule.

Alternatively or additionally to any of the embodiments above, the control unit includes an optical fiber and a ferrule disposed about the optical fiber.

Alternatively or additionally to any of the embodiments above, the optical fiber and the ferrule are configured to engage the second connector.

Alternatively or additionally to any of the embodiments above, the control unit includes a rotary motor.

Alternatively or additionally to any of the embodiments above, the imaging core and the connector assembly define a longitudinal axis, and wherein the rotary motor is laterally offset from the longitudinal axis.

Alternatively or additionally to any of the embodiments above, the control unit includes a common mode choke.

Alternatively or additionally to any of the embodiments above, the control unit includes a rotary transformer.

Alternatively or additionally to any of the embodiments above, the control unit includes an optical rotary joint.

An intravascular imaging system is disclosed. The intravascular imaging system comprises: an imaging catheter; an imaging core translatable and rotatable within the imaging catheter; wherein the imaging core includes an ultrasound transducer, a conductor coupled to and extending from the ultrasound transducer, an optical imaging device, and an optical fiber coupled to and extending from the optical imaging device; a connector assembly disposed adjacent to a proximal end region of the imaging catheter, the connector assembly being configured to connect the imaging catheter to a motor drive unit; and wherein the connector assembly includes an electrical connector configured to couple the conductor to the motor drive unit and an optical connector configured to couple the optical fiber to the motor drive unit.

Alternatively or additionally to any of the embodiments above, the electrical connector includes one or more electrical pins.

Alternatively or additionally to any of the embodiments above, the optical connector includes a ferrule disposed about the optical fiber and a connecting sleeve disposed about the ferrule.

Alternatively or additionally to any of the embodiments above, the motor drive unit includes a second optical fiber and a second ferrule disposed about the second optical fiber.

Alternatively or additionally to any of the embodiments above, the connecting sleeve is configured to engage the second ferrule.

A method for coupling an intravascular imaging device to a motor drive unit is disclosed. The method comprises: engaging a connector assembly of an imaging catheter to the motor drive unit; wherein an imaging core is translatable and rotatable within the imaging catheter; wherein the imaging core includes an ultrasound transducer, a conductor coupled to and extending from the ultrasound transducer, an optical imaging device, and an optical fiber coupled to and extending from the optical imaging device; and wherein the connector assembly includes an electrical connector configured to couple the conductor to the motor drive unit and an optical connector configured to couple the optical fiber to the motor drive unit.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
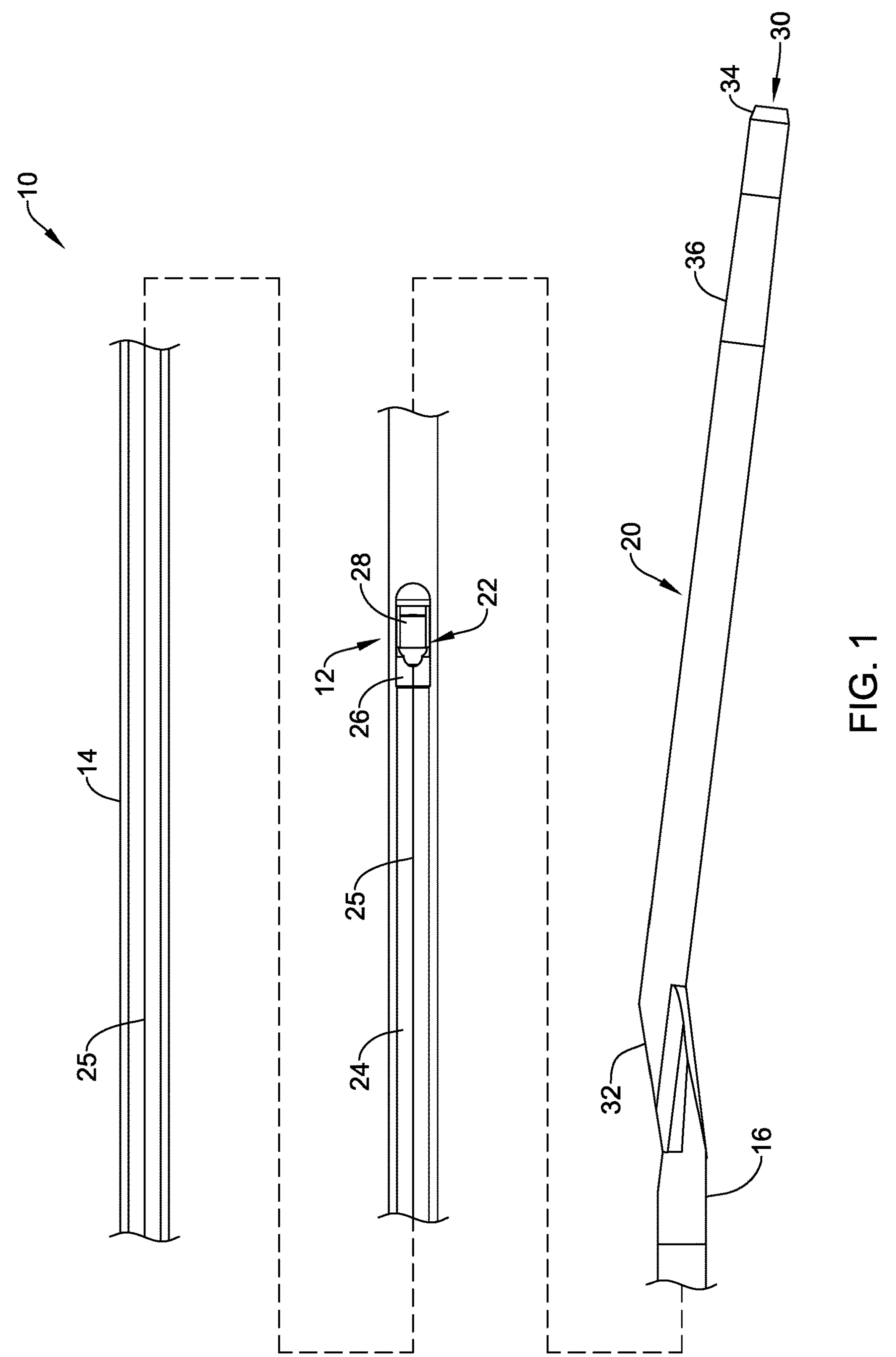
FIG. 1 is a partially cut away side view of an example medical device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a side view of a portion of example medical device 10. In at least some instances, the medical device 10 takes the form of an imaging medical device. For example, the medical device 10 may be an intravascular ultrasound (IVUS) device that may be used to image a blood vessel. In some of these and in other instances the medical device may be an optical coherence tomography (OCT) imaging device, a near-infrared spectroscopy (NIRS) imaging device, near-infrared fluorescence (NIRF) imaging device, a photoacoustic imaging device, a fluorescence-lifetime imaging device, combinations thereof (including combinations that include IVUS), and/or the like. In addition to be used for intravascular imaging, the medical device 10 may also be used for pulmonary procedures/imaging. The structure/form of the medical device 10 can vary. In some instances, the medical device 10 may include an elongate shaft 12 having a proximal end region 14 and a distal end region 16. A tip member 20 may be coupled to or otherwise disposed adjacent to the distal end region 16. The tip member 20 may include a guidewire lumen 30 having a guidewire exit port 32, an atraumatic distal end 34, one or more radiopaque markers 36, and/or other features. In some embodiments, the tip member 20 may extend at a non-parallel angle to the proximal end region 14 of the elongate shaft 12.

An imaging assembly 22 (e.g., which may sometime be referred to as an imaging core) may be disposed within a lumen of the elongate shaft 12. In general, the imaging core 22 may be used to capture/generate images of a blood vessel. In some instances, the medical device may include devices and/or features similar to those disclosed in U.S. Patent Application Pub. No. US 2012/0059241 and U.S. Patent Application Pub. No. US 2017/0164925, the entire disclosures of which are herein incorporated by reference. In at least some instances, the medical device 10 may resemble and/or include features that resemble the OPTICROSS™ Imaging Catheter, commercially available from BOSTON SCIENTIFIC, Marlborough, MA.

The imaging core 22 may include a drive shaft or cable 24, a housing 26, and an imaging member or transducer 28 coupled to the drive shaft 24 and/or housing 26. In at least some instances, the transducer 28 includes an ultrasound transducer. Other transducers are also contemplated. The transducer 28 may be rotatable and/or axially translatable relative to the elongate shaft 12. For example, the drive shaft 24 may be rotated and/or translated in order to rotate and/or translate the transducer 28 (and the housing 26). A conductor 25 may be coupled to the transducer and extend proximally therefrom. In some instances, the conductor 25 may take the form of a wire or cable (e.g., a coaxial cable) with suitable electrical conduction properties that allow the conductor 25 to energize the transducer 28. In some of these and in other instances, the conductor 25 may include a chip configured to improve the signal to noise ratio.

Figure 2:
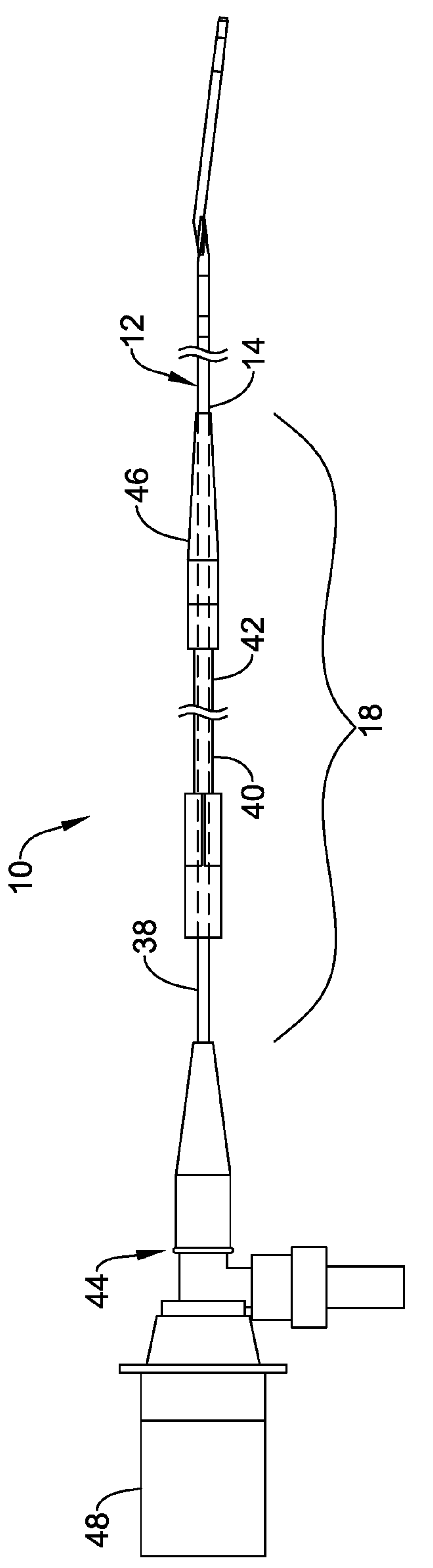
FIG. 2 is a side view of an example medical device.

The proximal end region 14 of the elongate shaft 12 may be coupled to a telescoping assembly 18 as shown in FIG. 2. In general, the telescoping assembly 18 may be configured to allow the medical device operator to move the drive shaft 24 including the imaging core 22 proximally and distally within the catheter (e.g., relative to the elongate shaft 12), without having to move the entire catheter within the patient. This allows the catheter operator to easily change the location of the imaging core 22 within the patient. For example, the telescoping assembly 18 may be actuated to change the location of the imaging core 22 within the elongate shaft 12.

The proximal end region 14 of the elongate shaft 12 may be coupled to the telescoping assembly 18. For example, the proximal end region 14 of the elongate shaft 12 may be coupled to a distal hub 46 of the telescoping assembly 18. A proximal hub 44 may be coupled to the telescoping assembly 18 (e.g., at the proximal end of the telescoping assembly 18). The drive shaft 24 (see FIG. 1) may extend through the telescoping assembly 18 and be coupled to and/or otherwise secured to the proximal hub 44. The proximal hub 44 may include a connector assembly 48. In general, the connector assembly 48 may allow the medical device 10 (e.g., the elongate shaft 12) to a control unit (e.g., a motor drive unit and/or the like) as described in more detail herein.

The telescoping assembly 18 may include a first sheath 38 and a second sheath 40. In some instances, the first sheath 38 may be understood to be an inner telescoping tube 38 and the second sheath 40 may be understood to be an outer telescoping tube 40. Generally, the outer telescoping tube 40 may be disposed over the inner telescoping tube 38. The inner telescoping tube 38 may be coupled to or otherwise secured to the proximal hub 44. The outer telescoping tube 40 may be coupled or otherwise secured to the distal hub 46. The inner telescoping tube 38 may be axially and/or rotatably moveable relative to the outer telescoping tube 40. Because the drive shaft 24 may be secured to the proximal hub 44 and/or the inner telescoping tube 38 and because the elongate shaft 12 may be secured to the distal hub 46, movement of the proximal hub 44 relative to the distal hub 46 results in movement of the inner telescoping tube 38 and the drive shaft 24 relative to the distal hub 46 and/or the elongate shaft 12.

Figure 3:
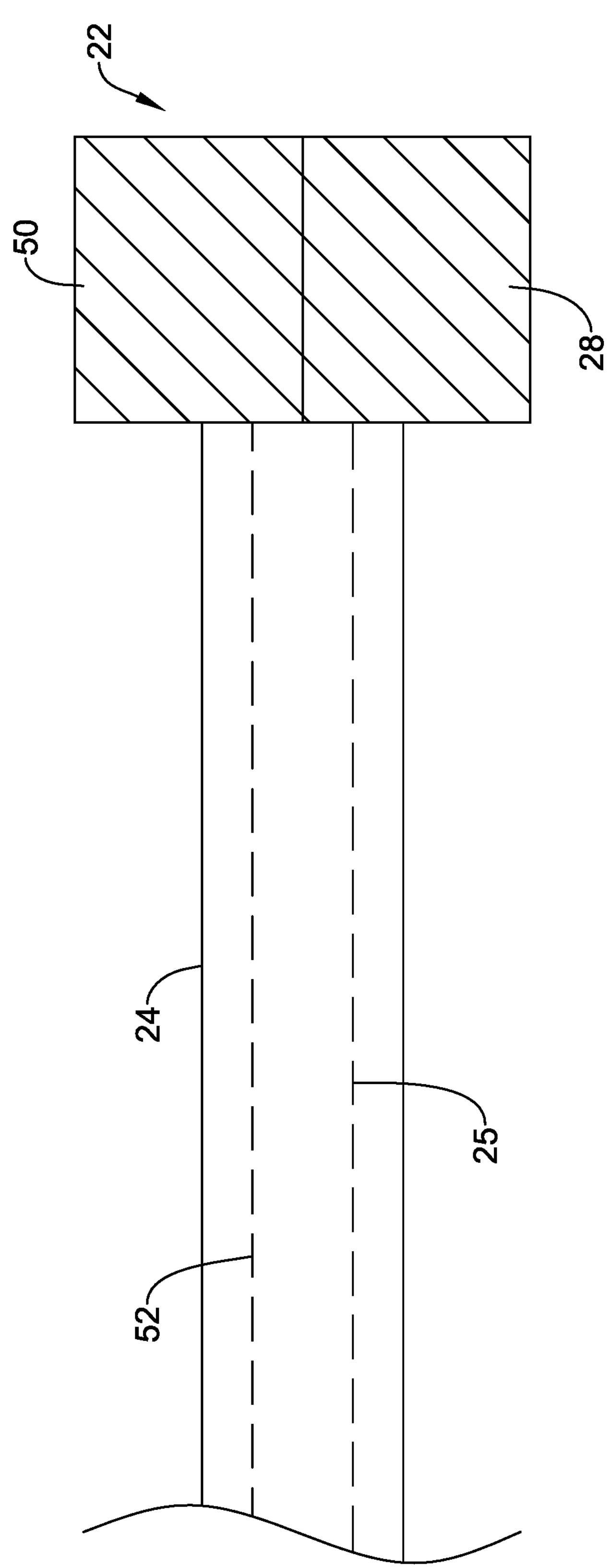
FIG. 3 is a schematic view of a portion of an example imaging core.

For some medical interventions, it may be desirable to have more than one type of imaging modality. For example, the imaging core 22 may include a first imaging device (e.g., the ultrasound transducer 28) and a second imaging device 50 as schematically depicted in FIG. 3. In this example, the second imaging device 50 may take the form of an optical imaging device. For example, the second imaging device 50 may be an OCT imaging device. In some of these and in other instances, the second imaging device 50 may include a NIRF imaging device that can signify fluorescence intensity as a function of angular position. Such information may be considered to be one-dimensional (e.g., the depth of the fluorescent signal within the tissue is unknown). Thus, the second imaging device 50 may provide additional fluorescent information that helps to enhance the two-dimensional IVUS image, rather than providing a separate two-dimensional image. Other imaging devices are contemplated including those disclosed herein.

Figure 4:
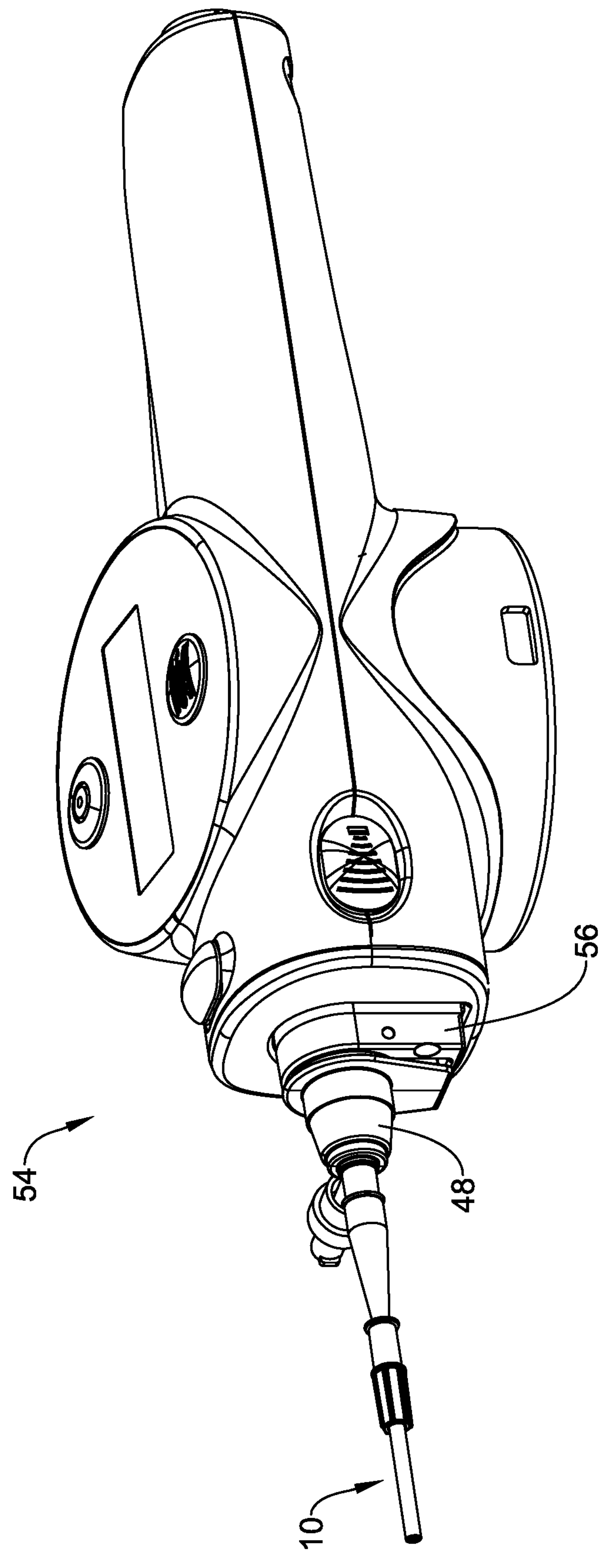
FIG. 4 is a perspective view of a portion of an example medical device system.

An optical fiber 52 may be coupled to the optical imaging device 50 and extend therefrom. It can be appreciated that in devices such as the medical device 10, the imaging core 22 may be rotated and translated relative to the shaft 12. In order to do so, the shaft 12 may be connected to a control unit such as a motor drive unit (e.g., a motor drive unit 54 as shown in FIG. 4). For example, FIG. 4 is a perspective view showing the medical device 10 coupled to a motor drive unit 54. For example, the connector assembly 48 may be coupled to a connector receptacle 56 on the motor drive unit 54. When doing so, the connector assembly 48 and the connector receptacle 56 may be configured so that both the first imaging device 28 and the second imaging device 50 may be coupled to the motor drive unit 54 in a manner that permits the rotation and translation of the imaging core 22 as well as the ability to power/energize the first imaging device 28 and the second imaging device 50. At least some details regarding the connections between the connector assembly 48 and the connector receptacle 56 that allow for rotation/translation as well as power/energy transmission are disclosed herein.

Figure 5:
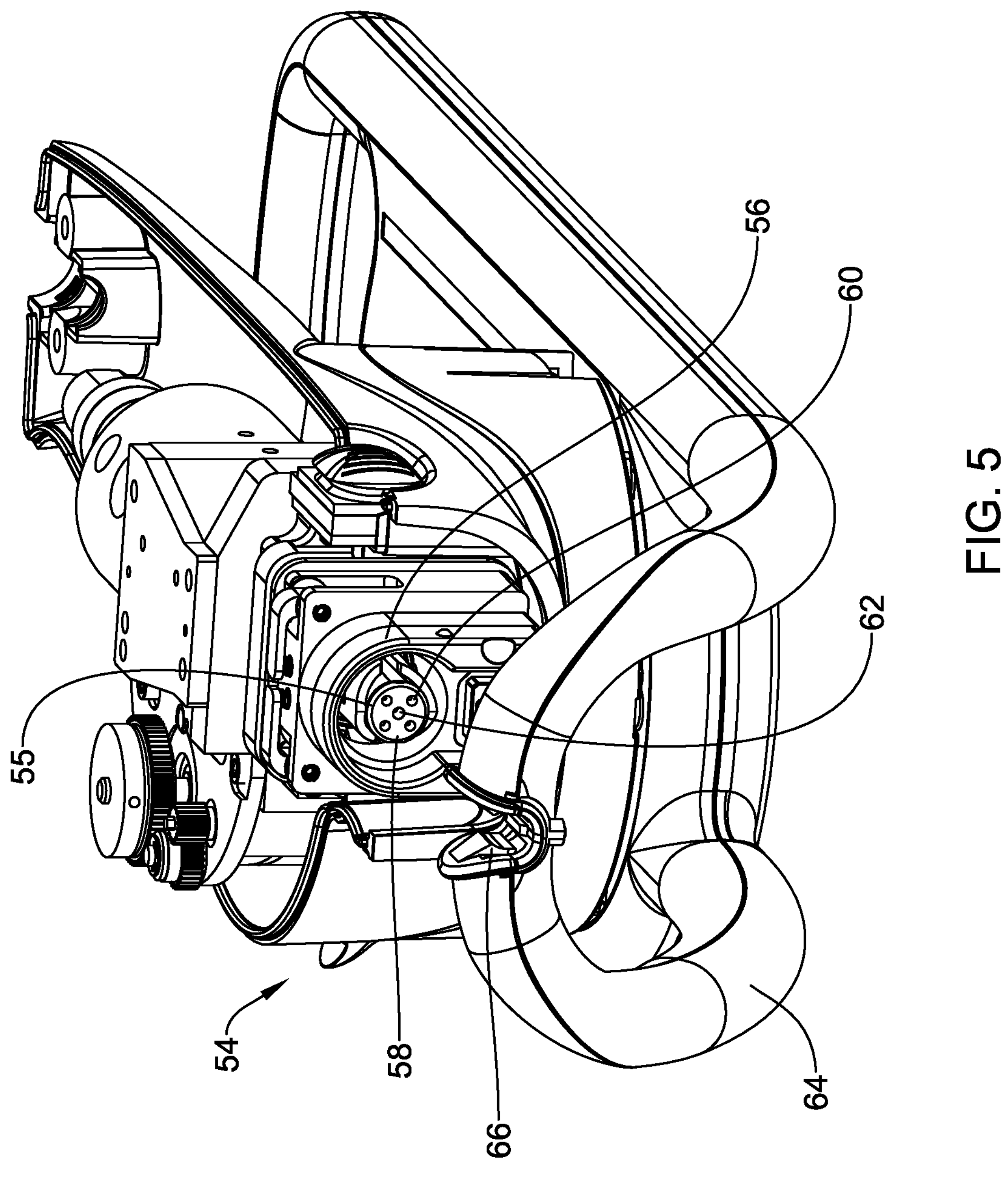
FIG. 5 is a perspective view of a portion of an example medical device system.

FIG. 5 is a partial cross-sectional view of the motor drive unit 54 with the medical device 10 disconnected therefrom. Here it can be seen that the connector receptacle 56 may include a connector interface 58. In general, the connector receptacle 56 is configured to receive the connector assembly 48 of the medical device 10. The connector interface 58 may be configured to engage with, for example, the electrical and optical connectors that may be part of the connector assembly 48. For example, the connector interface 58 may include a plurality of openings formed therein including one or more electrical pin openings/receptacles 60 and an optical connector opening/receptacle 62. The connector interface 58 may also include an orienting surface 55 (e.g., a cam surface) that is generally designed to help orient the connector assembly 48 in a suitable manner when engaging the connector assembly 48 with the connector receptacle 56. Also shown in FIG. 5 is that the motor drive unit 54 may be coupled to (e.g., slidably coupled to) a translation base or sled 64. The sled 64 may include a catheter cradle region 66 that may be configured to help support the medical device 10 and/or help to keep the elongate shaft 12 stationary during a pullback procedure.

Figure 6:
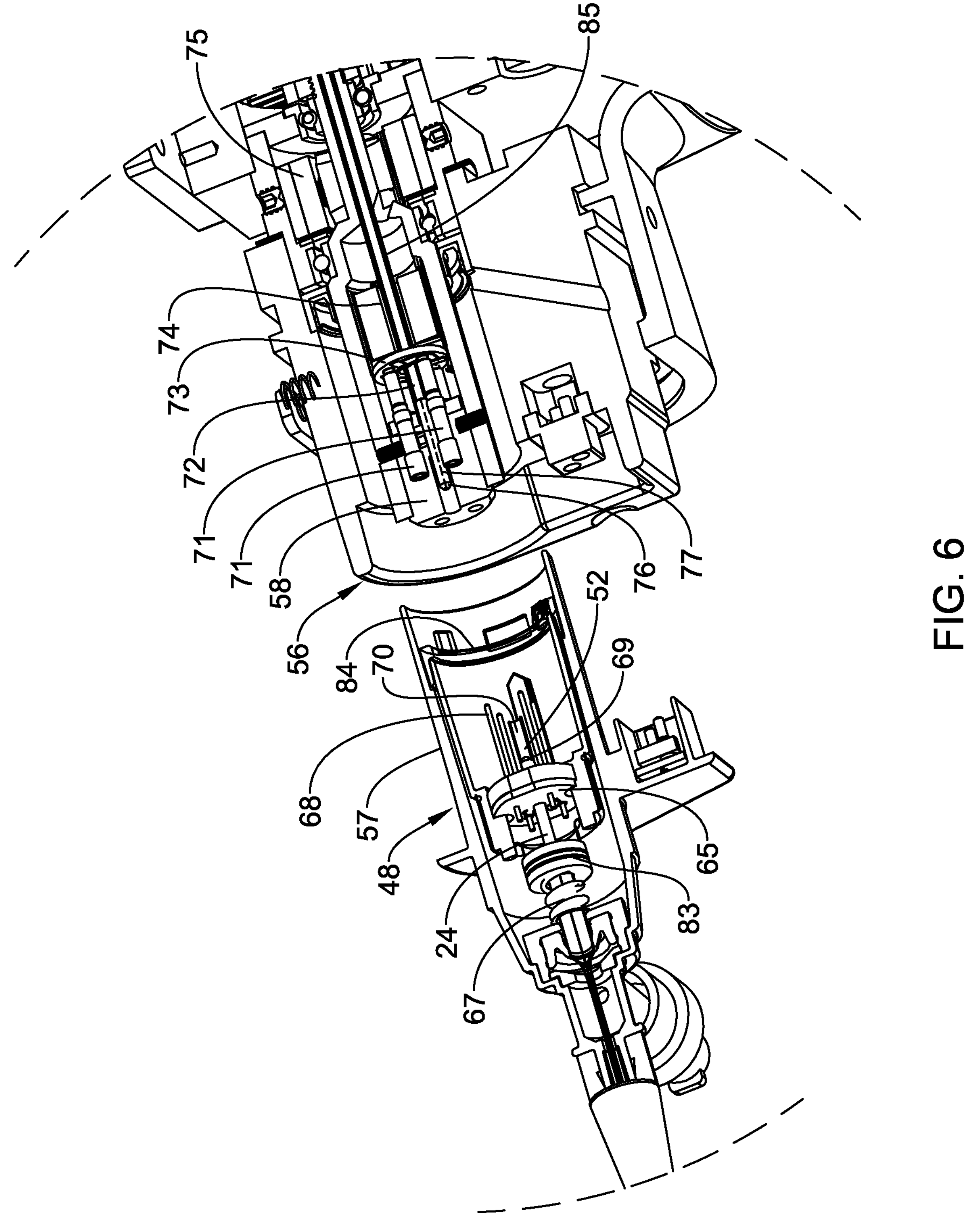
FIG. 6 is a partial cross-sectional view of a portion of an example medical device system.

FIG. 6 depicts the connector assembly 48 prior to connecting to the connector receptacle 56. Here it can be seen that the connector assembly 48 may include an interface plate 65, which may include a printed circuit board. The printed circuit board 65 may be coupled to the drive shaft 24 and include electrical connections with the conductor 25 (e.g., and/or the imaging core 22 and/or the drive shaft 24). A thrust bearing 83 may be disposed adjacent to the printed circuit board 65. The thrust bearing 83 may help to reduce friction (e.g., when the imaging core 22 and/or the drive shaft 24 are rotated). A spring or biasing member 67 may be disposed adjacent to the thrust bearing 83. The spring 67 may be configured to bias/shift the position of the thrust bearing 83 and/or the printed circuit board 65 within the housing 57 of the connector assembly 48. In other words, the printed circuit board 65 (e.g., and various structural components coupled thereto) may be movable within the housing 57 of the connector assembly 48 and the spring 67 may tend to urge the printed circuit board 65 in the direction of the connector receptacle 56 (e.g., toward the proximal end of the connector assembly 48). Because of this, the connector assembly 48 may be considered to be spring-loaded. A retaining sleeve 84 may be disposed within the housing 57. The retaining sleeve 84 may help to retain the printed circuit board 65 (and/or components coupled thereto) within the housing 57.

Figure 7:
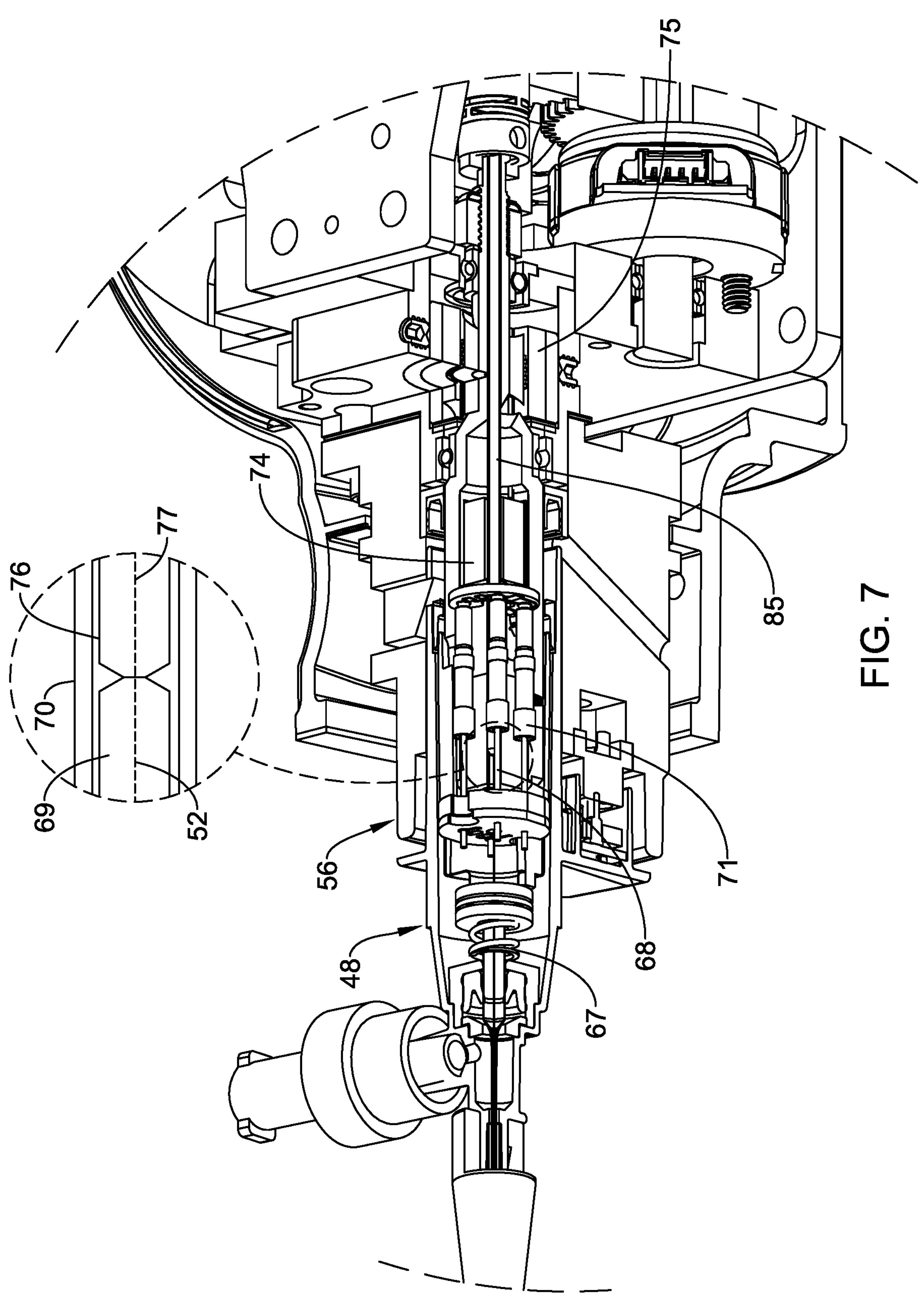
FIG. 7 is a partial cross-sectional view of a portion of an example medical device system.

A spring-loaded connection between the connector assembly 48 and the connector receptacle 56 may be desirable for a number of reasons. For example, the spring-loaded connection may provide a spring force onto the optical fiber 52. This helps to urge the optical fiber 52 toward the connector receptacle 56 and allow for contact between the optical fiber 52 and an optical fiber (e.g., the optical fiber 77 as shown in FIG. 7) within the motor drive unit 54. Furthermore, the spring-loaded connection allows for contact between the optical fibers 52, 77 (see, for example, FIG. 7) without having to bend the optical fiber 52. For example, if the optical fiber 52 (and/or the connector assembly 48) was not spring-loaded, the optical fiber 52 may need to be bent when being brought into and out of connection with the optical fiber 77. Bending may undesirably impact the light transmission along the optical fiber 52 and/or the transmission between the optical fibers 52, 77. It can be appreciated that the spring-loaded connection allows for components of the motor drive unit 54 (e.g., such as the optical fiber 77, the ferrule 76, the optical rotary joint 81; please see FIG. 7) to remain in place (e.g., remain axially stationary) when connecting the connector assembly 48 with the connector receptacle 56. Finally, the spring-loaded connection allows for the imaging core 22 (including the optical fiber 52) to translate as a singular unit, for example during a pullback procedure.

One or more electrical connectors or pins 68 may project from the printed circuit board 65. In general, the pins 68 are configured to help communicate and/or transfer electrical signals and/or electrical power between the medical device 10 and the motor drive unit 54. For example, the pins 68 may help to communicate electrical signals between the transducer 28 and suitable electronics within or adjacent to the motor drive unit 54 in order to power the transducer 28. In addition, one or more optical connector structures may also project from and/or extend through the printed circuit board 65. For example, a ferrule 69 may be coupled to the optical fiber 52 (e.g., which may extend through the printed circuit board 65) and project from the printed circuit board 65. A connecting sleeve 70 may be disposed about the ferrule 69.

The connector interface 58 may be coupled to a plurality of pin receptacles 71. In some instances, the pin receptacles may take the form of spring-loaded electrical connectors (e.g., pogo pins). The pin receptacles 71 may extend to another printed circuit board 73, which is connected to other electrical components. For example, the printed circuit board 73 may be coupled to a common mode choke 74 (e.g., a ferrite choke). The common mode choke 74 may help to reduce noise in the system. The common mode choke 74 may be coupled to a rotary transformer 75. The rotary transformer 75 may be connected to additional hardware and/or include a suitable connector for connecting the rotary transformer 75 to suitable hardware, for example powering and/or energizing the transducer 28. The form of the common mode choke 74 and the rotary transformer 75 may vary. In some instances, the common mode choke 74 may be positioned elsewhere within the motor drive unit 54. In still other instances, the common mode choke 74 may be considered to be optional. As can also be seen in FIG. 6, a ferrule 76 may be disposed within and/or extend through the connector interface 58. An optical fiber 77 may be disposed within the ferrule 76. A tube 85 may extend about the optical fiber 77 and extend through the common mode choke 74 and the rotary transformer 75. The tube 85 may help to contain the optical fiber 77 and/or facilitate assembly of the system. These are just examples. Other rotational components are contemplated.

FIG. 7 illustrates the connector assembly 48 coupled to the connector receptacle 56. Here it can be seen that the electrical pins 68 may be engaged with the pin receptacles 71. In addition, the optical fiber 52 may be brought into close engagement with the optical fiber 77. This may be aided by the connecting sleeve 70 helping to align the ferrules 69, 76 (and, thus, optical fibers 52, 77). The spring 67 may help to urge the connector assembly 48 toward the connector receptacle 56, for examples, so that the optical fibers 52, 77 may be brought into close contact in order to efficiently transmit light therebetween. Thus, the spring-loaded connection between the connector assembly 48 and the connector receptacle 56 may desirably impact the connection between the optical fibers 52, 77.

Figure 8:
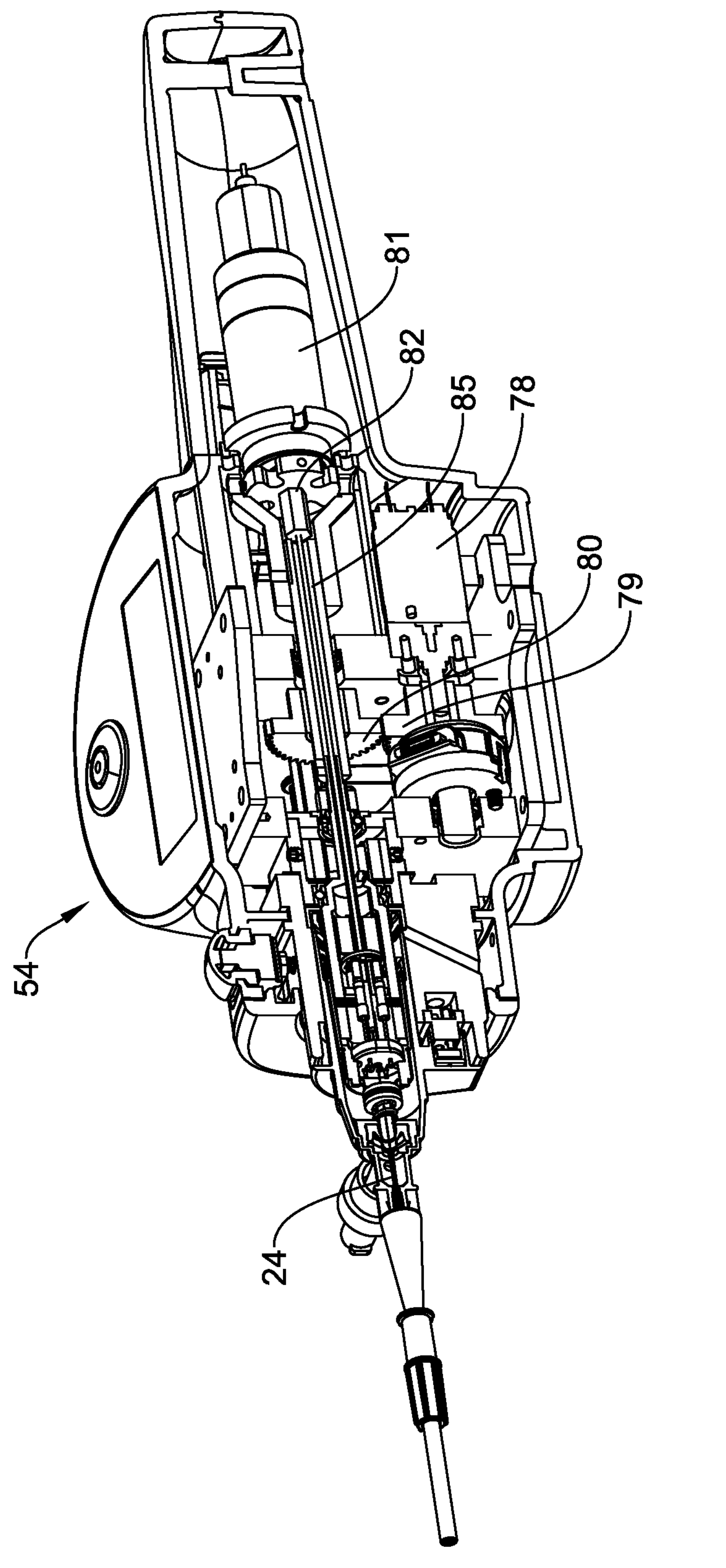
FIG. 8 is a partial cross-sectional view of a portion of an example medical device system.

FIG. 8 is another view of the motor drive unit 54 that helps to show additional components. For example, a rotary motor 78 may be disposed within the motor drive unit 54. In general, the rotary motor 78 may be configured to rotate the drive shaft 24 (and/or the imaging core 22). In this example, rotary motor 78 is offset from the axis of the drive shaft 24 (and/or the imaging core 22). In other words, the drive shaft 24 (and/or the imaging core 22) may define a longitudinal axis, and the rotary motor 78 may be laterally offset from the longitudinal axis. Other arrangements are contemplated including arrangements where the drive shaft 24*d* and the rotary motor 78 are axially aligned. One or more gears 79, 80 may be used to coupled the rotary motor 78 to the drive shaft 24.

The motor drive unit 54 may also include an optical rotary joint (e.g., a fiber optic rotary joint) 81. The optical rotary joint 81 may be coupled to the tube 85 (e.g., and/or the optical fibers 52, 77). This may include attaching the tube 85 to a rotatable plate 82. The optical rotary joint 81 may be connected to or otherwise include connectors suitable for connecting the optical rotary joint 81 to additionally hardware such a light source (e.g., a laser), an interferometer, and/or the like.

Figure 9:
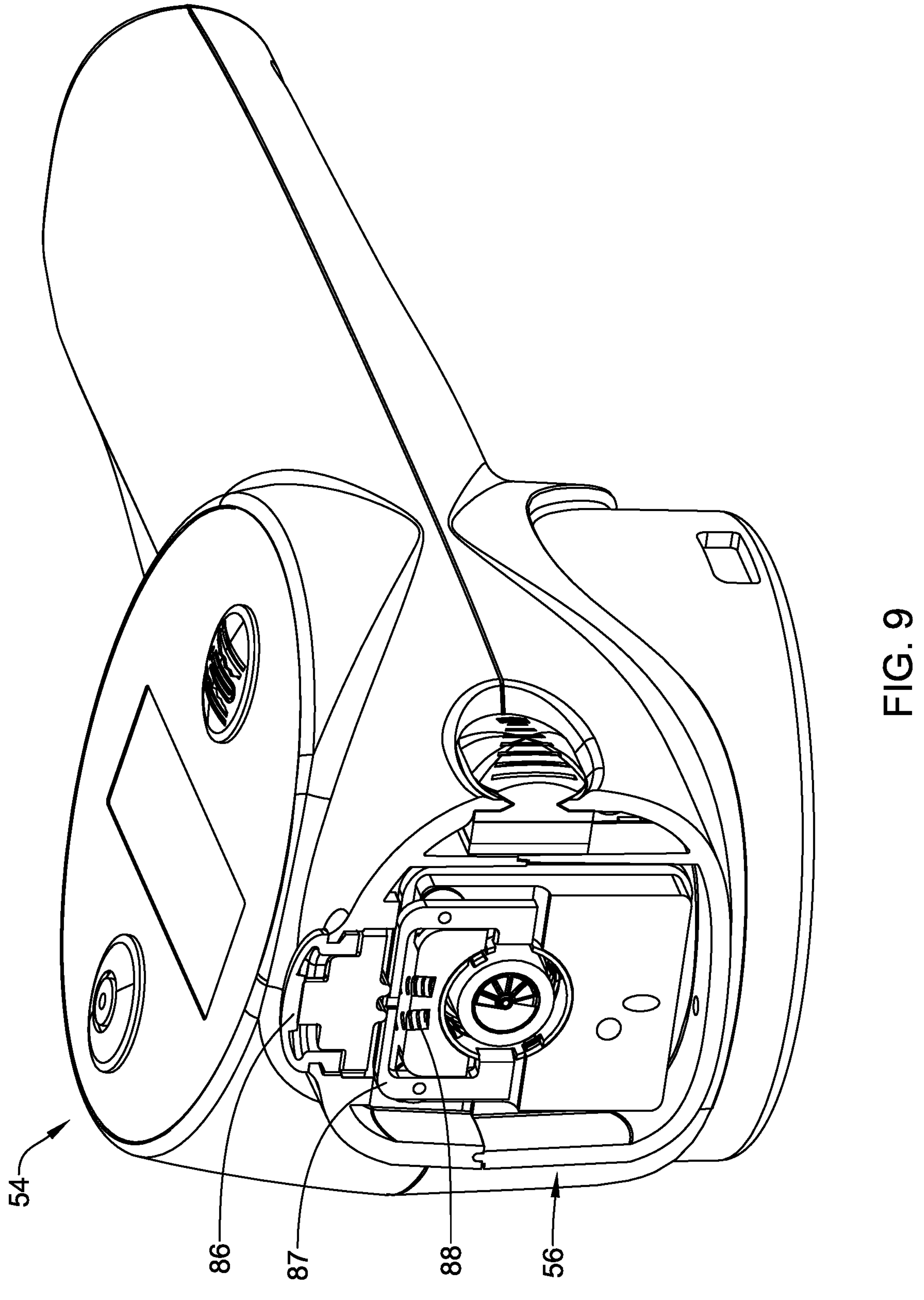
FIG. 9 is a partially cut away perspective view of a portion of an example medical device system.

FIG. 9 illustrates is another partially cutaway view of the motor drive unit 54, which depicts that the motor drive unit 54 may include one or more connector/actuators 86 that help to releasably secure the connector assembly 48 to the connector receptacle 56. The connector/actuators 86 may include a latch or securing member 87. The latch 87 may engage the connector assembly 48 in a manner that may securely hold the connector assembly 48 to the connector receptacle 56. A biasing member or spring 88 may be coupled to the latch 87. The spring 88 may bias the latch 87 into engagement with the connector assembly 48. Actuating the connector/actuator 86 may overcome the bias to release the connection between the connector assembly 48 to the connector receptacle 56.

The materials that can be used for the various components of the medical device 10 (and/or other guidewires disclosed herein) and the various tubular members disclosed herein may include those commonly associated with medical devices. For example, the medical device 10 and/or other components thereof be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-clastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

In at least some embodiments, portions or all of the medical device 10 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the medical device 10 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the medical device 10 to achieve the same result.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An intravascular imaging system, comprising:

an imaging catheter;

an imaging core translatable and rotatable within the imaging catheter;

wherein the imaging core includes a first imaging device and a second imaging device different from the first imaging device;

wherein the imaging catheter includes a connector assembly disposed adjacent to a proximal end region of the imaging catheter, the connector assembly being configured to connect the imaging catheter to a control unit;

wherein the connector assembly includes a spring and a thrust bearing;

wherein the connector assembly includes a first connector for connecting the first imaging device to the control unit and a second connector for connecting the second imaging device to the control unit; and wherein the spring is configured to bias the thrust bearing toward a connector receptacle of the control unit such that connector assembly is spring-loaded.

2. The intravascular imaging system of claim 1, wherein the first imaging device includes an ultrasound transducer.

3. The intravascular imaging system of claim 2, further comprising an electrical conductor coupled to the ultrasound transducer and extending to the first connector.

4. The intravascular imaging system of claim 2, wherein the first connector includes one or more electrical pins.

5. The intravascular imaging system of claim 1, wherein the second imaging device includes an optical imaging device.

6. The intravascular imaging system of claim 5, further comprising an optical fiber coupled to the optical imaging device and extending to the second connector.

7. The intravascular imaging system of claim 5, wherein the second connector includes a ferrule and a connecting sleeve disposed about the ferrule.

8. The intravascular imaging system of claim 1, wherein the control unit includes an optical fiber and a ferrule disposed about the optical fiber.

9. The intravascular imaging system of claim 8, wherein the optical fiber and the ferrule are configured to engage the second connector.

10. The intravascular imaging system of claim 1, wherein the control unit includes a rotary motor.

11. The intravascular imaging system of claim 10, wherein the imaging core and the connector assembly define a longitudinal axis, and wherein the rotary motor is laterally offset from the longitudinal axis.

12. The intravascular imaging system of claim 1, wherein the control unit includes a common mode choke.

13. The intravascular imaging system of claim 1, wherein the control unit includes a rotary transformer.

14. The intravascular imaging system of claim 1, wherein the control unit includes an optical rotary joint.

15. An intravascular imaging system, comprising:

an imaging catheter;

an imaging core translatable and rotatable within the imaging catheter;

wherein the imaging core includes an ultrasound transducer, a conductor coupled to and extending from the ultrasound transducer, an optical imaging device, and an optical fiber coupled to and extending from the optical imaging device;

wherein the imaging catheter includes a connector assembly disposed adjacent to a proximal end region of the imaging catheter, the connector assembly being configured to connect the imaging catheter to a motor drive unit;

wherein the connector assembly includes an electrical connector configured to couple the conductor to the motor drive unit and an optical connector configured to couple the optical fiber to the motor drive unit; and wherein the connector assembly includes a thrust bearing and a biasing member configured to bias the thrust bearing toward the connector receptacle of the control unit.

16. The intravascular imaging system of claim 15, wherein the electrical connector includes one or more electrical pins.

17. The intravascular imaging system of claim 15, wherein the optical connector includes a ferrule disposed about the optical fiber and a connecting sleeve disposed about the ferrule.

18. The intravascular imaging system of claim 17, wherein the motor drive unit includes a second optical fiber and a second ferrule disposed about the second optical fiber.

19. The intravascular imaging system of claim 18, wherein the connecting sleeve is configured to engage the second ferrule.

20. The intravascular imaging system of claim 1, wherein a printed circuit board is coupled to the drive shaft.

* * * * *